(12) United States Patent
Cadieu et al.

(10) Patent No.: US 10,470,677 B2
(45) Date of Patent: Nov. 12, 2019

(54) ARTIFICIALLY INTELLIGENT EJECTION FRACTION DETERMINATION

(71) Applicant: Bay Labs, Inc., San Francisco, CA (US)

(72) Inventors: Charles Cadieu, San Francisco, CA (US); Michael G. Cannon, Haverford, PA (US); Ha Hong, Pleasant Hill, CA (US); Kilian Koepsell, San Francisco, CA (US); Johan Mathe, San Francisco, CA (US); Nicolas Poilvert, Seattle, WA (US)

(73) Assignee: BAY LABS, INC., San Francisco, CA (US)

( * ) Notice: Subject to any disclaimer, the term of this patent is extended or adjusted under 35 U.S.C. 154(b) by 181 days.

(21) Appl. No.: 15/730,377

(22) Filed: Oct. 11, 2017

(65) Prior Publication Data

US 2019/0104949 A1 Apr. 11, 2019

(51) Int. Cl.
*A61B 5/029* (2006.01)
*G06T 7/00* (2017.01)
(Continued)

(52) U.S. Cl.
CPC .............. *A61B 5/029* (2013.01); *G06N 3/08* (2013.01); *G06T 7/0012* (2013.01); *G16H 50/20* (2018.01)

(58) Field of Classification Search
CPC .... A61B 5/029; A61B 5/02028; G16H 50/20; G16H 50/30; G06T 7/0012
See application file for complete search history.

(56) References Cited

U.S. PATENT DOCUMENTS

| 6,368,285 B1* | 4/2002 | Osadchy | .............. A61B 5/0064 382/131 |
|---|---|---|---|
| 2014/0029859 A1* | 1/2014 | Libin | ................. G06K 9/00221 382/224 |

(Continued)

FOREIGN PATENT DOCUMENTS

CN 106503610 3/2017

OTHER PUBLICATIONS

Lou et al. "A novel left ventricular volumes prediction method based on deep learning network in cardiac MRI." 2016 Computing in Cardiology Conference. Sep. 11, 2016. 89-92.
(Continued)

*Primary Examiner* — Alyssa M Alter
(74) *Attorney, Agent, or Firm* — Steven M. Greenberg, Esq.; Shutts & Bowen LLP

(57) ABSTRACT

Embodiments of the invention provide a method, system and computer program product for artificially intelligent ejection fraction determination. In a method for artificially intelligent ejection fraction determination, a neural network is loaded into memory of a computer, that has been trained with different sets of cardiac imaging data acquired during imaging of a ventricle for different hearts and a known ejection fraction for each of the sets. Then, a contemporaneous set of imaging data is acquired of a ventricle of a heart and the contemporaneous set of imaging data is provided to the neural network. Finally, an ejection fraction determination output by the neural network is displayed in a display of the computer without tracing a ventricle boundary of the heart.

18 Claims, 1 Drawing Sheet

(51) Int. Cl.
*G06N 3/08* (2006.01)
*G16H 50/20* (2018.01)

(56) References Cited

U.S. PATENT DOCUMENTS

2014/0272842 A1* 9/2014 Kwiatkowski ........... G09B 7/00
　　　　　　　　　　　　　　　　　　　　　434/236
2017/0109881 A1* 4/2017 Avendi ................. G06T 7/0012

OTHER PUBLICATIONS

Lou et al. "Cardiac left ventricular volumes prediction method . . . " IEEE International Conference on Bioinformatics and Biomedicine. Dec. 15, 2016. 1604-1610.
Kabani et al."Estimating Ejection Fraction and Left Ventricle Volume Using Deep Convolutional Networks." MICCAI 2015.Jul. 1, 2016.
Ira Korshunova. "Diagnosing Heart Diseases with Deep Neural Networks." Mar. 15, 2016. http://irakorshunova.github.io/2016/03/15/heart.html.
Florian Muellerklein. "Measuring cardiac ejection fraction with deep convolution neural networks." Mar. 17, 2016. http://florianmuellerklein.github.io/DSB/.
Wang et al. "Diagnosis of Heart Disease via CNNs." Mar. 24, 2016. http://cs231n.stanford.edu/reports/2016/pdfs/331_Report.pdf.

* cited by examiner

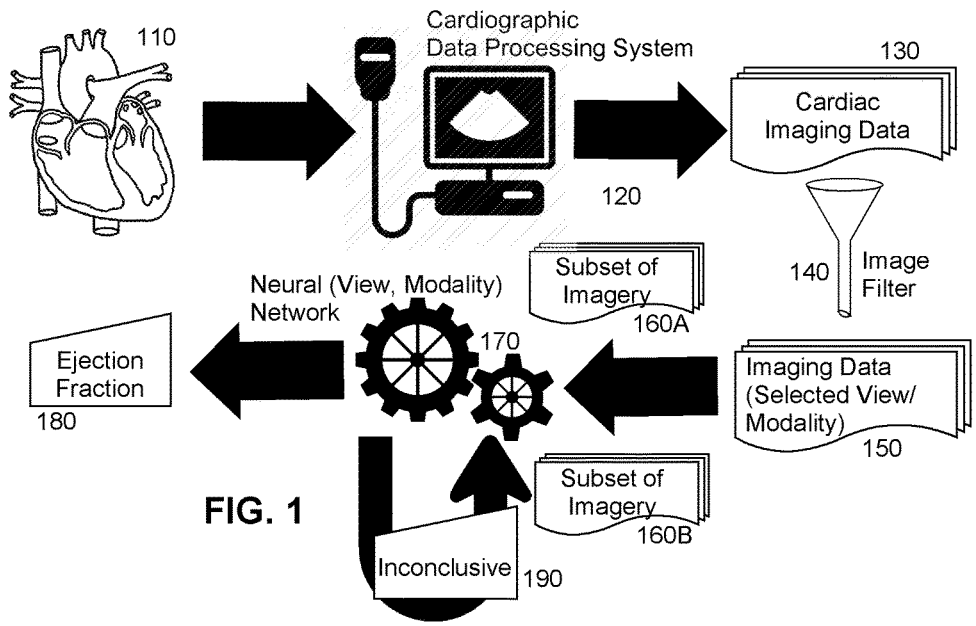
FIG. 1
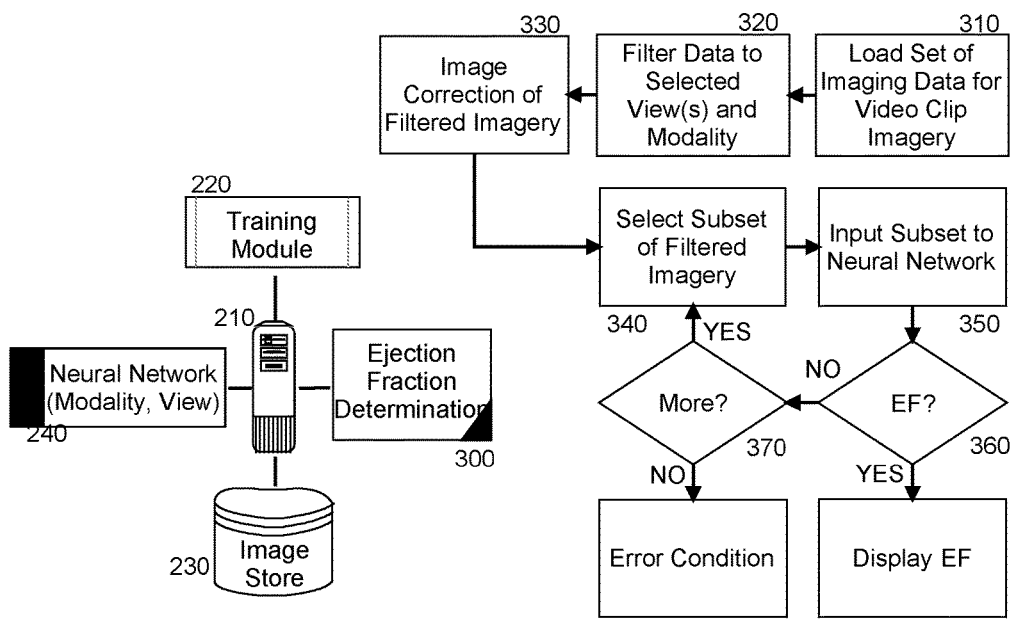
FIG. 2
FIG. 3

ARTIFICIALLY INTELLIGENT EJECTION FRACTION DETERMINATION

BACKGROUND OF THE INVENTION

Field of the Invention

The present invention relates to the systolic function of the heart and more particularly ejection fraction measurement.

Description of the Related Art

The ejection fraction is a measurement of the systolic function of the heart that refers to the percentage of blood leaving the heart at each contraction. Specifically, during each pumping cycle of the heart, the heart both contracts and also relaxes. When the heart contracts, the heart ejects blood from its two pumping chambers, known as the left ventricle and the right ventricle. Conversely, when the heart relaxes, both ventricles refill with blood. Of note, no matter how forceful the contraction of the heart, the heart is not able to pump all of the blood out of each ventricle. Instead, some blood remains. Hence, the term "ejection fraction" refers to the percentage of blood that is able to be pumped out of a filled ventricle with each heartbeat.

Of the two ventricles, the left ventricle is the main pumping chamber of the heart that pumps oxygenated blood through the ascending aorta to the rest of the body, and the right ventricle is the chamber that pumps blood to the lungs for oxygenation. The ejection fraction of the left or right ventricle may be measured through the use of several different imaging techniques. The most common technique is the echocardiogram in which the ejection fraction is measured by sound-wave produced images of the heart and the blood pumping through the heart. Other alternatives to echocardiography include the use of magnetic resonance imaging (MRI), computerized tomography (CT) and nuclear medicine scanning, catheter-based imaging.

Current ejection fraction measurement methods tend to inaccurately assess disease conditions of the heart. This error can lead to the delayed treatment of patients, and the significant worsening of disease conditions during the delay. In this regard, echocardiography relies upon Simpson Biplane methodology to produce a measurement. In particular, in the Simpson Biplane methodology, the end systolic and end diastolic volumes of the ventricle are measured so as to compute a fractional difference. But, in doing so, the ventricle border needs to be manually traced by a human reader, which is subjective to the person. Then, the ventricle volume is assumed to be composed of a finite number, usually twenty, of elliptical cylinders, which while convenient, is not accurate. Moreover, this methodology relies on finding the exact end systolic and end diastolic image frames, often nontrivial step that can introduce errors if not done accurately. As a result, current methods in ejection fraction measurement perform measurements in a way that is neither optimized nor reproducible despite the advances in modern diagnostic technologies.

BRIEF SUMMARY OF THE INVENTION

Embodiments of the present invention address deficiencies of the art in respect to ejection fraction measurement and provide a novel and non-obvious method, system and computer program product for artificially intelligent ejection fraction determination. In an embodiment of the invention, a method for artificially intelligent ejection fraction determination includes training a neural network with different sets of cardiac imaging data acquired of a ventricle for different hearts and a known ejection fraction for each of the sets. Then, the trained neural network is loaded into memory of a computer. A contemporaneous set of imaging data is acquired of a ventricle of a heart whether in the form of clip imagery or data produced during the imaging process of the ventricle of the heart ultimately which is transformed into spatial data of the heart over time that is able to be visualized in a display. Thereafter, the contemporaneous set of imaging data is provided to the neural network. Finally, an ejection fraction determination output by the neural network is displayed in a display of the computer without having traced the ventricle boundary of the heart.

In one aspect of the embodiment, the acquired contemporaneous set of imaging data is filtered to include only imaging data acquired utilizing a specified modality of imaging and representing a specific view of the ventricle. As well, in another aspect of the embodiment, only a portion of the contemporaneous set of imaging data is provided to the neural network and, upon receiving an indication from the neural network of an inconclusive output, an additional portion of the contemporaneous set of imaging data is provided to the neural network in order to receive a conclusive ejection fraction output from the neural network. In yet another aspect of the embodiment, a multiplicity of different neural networks each are trained with different sets of cardiographic imaging data acquired of the ventricle for different hearts and a known ejection fraction for each of the sets utilizing respectively different views and modalities. As such, only a particular one or more of the trained neural networks is loaded into the memory of the computer corresponding to an identified modality and at least one specified view of the contemporaneous set of imaging data. Finally, in even yet another aspect of the embodiment, the contemporaneous set of imaging data, in the form of video clip imagery, is pre-processed through re-sizing and cropping of each video clip of the imagery.

In another embodiment of the invention, a cardiographic data processing system is configured for artificially intelligent ejection fraction determination. The system includes a host computing platform that includes one or more computers each with memory and at least one processor. The system also includes an ejection fraction determination module. The module includes computer program instructions enabled upon execution in the memory of the host computing platform to load into the memory a neural network trained with different sets of cardiac imaging data acquired of a ventricle for different hearts and a known ejection fraction for each of the sets, to acquire a contemporaneous set of imaging data of a ventricle of a heart, to provide the contemporaneous set of imaging data to the neural network and to display in a display of the computer an ejection fraction determination output by the neural network without tracing the ventricle border of the heart.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein:

FIG. 1 is pictorial illustration of a process for artificially intelligent ejection fraction determination;

FIG. 2 is a schematic illustration of a cardiographic data processing system configured for artificially intelligent ejection fraction determination; and, FIG. 3 is a flow chart illustrating a process for artificially intelligent ejection fraction determination.

DETAILED DESCRIPTION OF THE INVENTION

Embodiments of the invention provide for artificially intelligent ejection fraction determination. In accordance with an embodiment of the invention, different sets of cardiac imaging data in the form of different video clips are acquired of the ventricle, left, right or both, for different hearts and a known ejection fraction corresponding to each of the sets is associated with the sets. The sets are then supplied as training input to a neural network with respect to the associated ejection fractions so as to train the neural network. In this regard, the sets are supplied as training input to the neural network in connection with a particular modality utilized to acquire the video clips, such as ultrasound echocardiography, CT or MRI, along with an indication of a particular type of view presented in each of the video clips, for instance parasternal long and short axis, apical two, three, four and five chamber and sub-coastal views. The neural network as trained may then be stored in connection with the particular modality and view.

Thereafter, a contemporaneous set of cardiac imaging data of a ventricle of a heart is acquired and a modality and view are identified for the contemporaneous set of imagery. Optionally, video clips determined to be of sub-standard quality are removed from the set. Then, a neural network is selected that corresponds to the identified modality and view of the contemporaneous set of imagery and the contemporaneous set of imagery is provided to the selected neural network so as to receive an ejection fraction value as output from the selected neural network without tracing the ventricle border of the heart. In this way the ejection fraction of the ventricle may be determined without reliance upon the traditional manual tracing of the ventricle by a human reader, manual determination of end systole or diastole frames, or a false presumption of modeling the ventricle volume with elliptical cylinders.

In further illustration, FIG. 1 is pictorial illustration of a process for artificially intelligent ejection fraction determination. As shown in FIG. 1, a cardiographic data processing system 120 acquires imaging data 130 of a ventricle of a heart 110 during imaging of the ventricle of the heart 110. The imaging data 130 may be acquired according to one or more different modalities, such as imaging data ultrasonically acquired, CT imagery or MRI imagery. The imaging data also may include spatial data over time, either one-dimensional, two dimensional or three-dimensional, from many different views of the heart 110 including parasternal long and short axis, apical two, three, four and five chamber and sub-coastal views. The video clip imagery 130 is then pre-processed so as to filter the imaging data 130 to a selection of imaging data 150 corresponding to one or more selected views of the heart 110 acquired by way of one or more selected modalities, for example either a two chamber or four chamber view of appropriate quality including omitting partial views or off-angle views, acquired by way of B-mode echocardiography, Doppler mode echocardiography, M-mode echocardiography, CT or MRI.

Then, a subset 160A of the selection of imaging data 150 are provided as input to a neural network 170 that had been previously training in connection with a selection of different views and modalities of ventricles of hearts and corresponding known ejection fractions for those different views. To the extent that the neural network outputs an inconclusive result 190, a new subset 160B of the selection of imaging data 150 is selected and provided to the neural network 170. This process may continue until no imaging data in the selection of imaging data 150 remain, or until the neural network 170 outputs an ejection fraction 180. In that instance, the ejection fraction 180 is displayed in a display for review by the end user. Optionally, the output of the neural network 170 may instead be stored in connection with a picture archiving and communication system (PACS), an electronic medical record (EMR) system, or a echocardiography/radiology information management system The process described in connection with FIG. 1 may be implemented in a cardiographic data processing system. In yet further illustration, FIG. 2 schematically shows a cardiographic data processing system configured for artificially intelligent ejection fraction determination. The system includes a host computing platform 210 that may include one or more computers, each with memory and at least one processor. A neural network 240 is loaded into memory of the host computing platform 210 that has been trained using training module 220 with input of a set of video clip imagery of different hearts each with a known ejection fraction. Optionally, the neural network 240 may include a selection of different neural networks, each trained with a different video clip imagery acquired according to different modalities and presenting different views of the heart.

Of note, an ejection fraction determination module 300 is provided. The ejection fraction determination module 300 includes computer program instructions that when executed in the memory of the host computing platform 210, is enabled to process a contemporaneously acquired selection of imaging data of a heart stored in image store 230. The program instructions are further enabled to pre-process the selection of imaging data by filtering the imaging data to only imaging data of a selected view sourced of a particular modality. The program instructions are yet further enabled to pre-process the imaging data, when in the form of video clip imagery, to crop the video clip imagery so as to remove extraneous material unrelated to the heart from the video clip imagery, and to rotate the video clip imagery to a correct angular orientation and to resize the video clip imagery.

In one aspect of the embodiment, the entirety of the filtered and pre-processed imaging data may be submitted to the neural network 240 for a determination of an ejection fraction. In this regard, on submission, each video clip in the contemporaneous set of video clip imagery is decomposed into a multiplicity of frames and the frames are submitted, in parallel, to the neural network 240. However, as an alternative, the program instructions may be enabled to select only a portion of the filtered and pre-processed imaging data for submission to the neural network 240 with imaging data for each video clip in the portion being decomposed into a multiplicity of frames and the frames being submitted, in parallel, to the neural network 240. In either circumstance, the program instructions are enabled to display an ejection fraction produced by the neural network 240 when provided by the neural network 240. However, in response to the condition when the neural network 240 produces an inconclusive result, the program instructions are enabled to select an additional portion of the filtered and pre-processed images for additional submission to the neural network 240 in a follow-on attempt at determining the ejection fraction of the ventricle of the heart.

In even yet further illustration of the operation of the ejection fraction determination module 300, FIG. 3 is a flow chart illustrating a process for artificially intelligent ejection fraction determination. Beginning in block 310, imaging data in the form of a set of video clip imagery of the ventricle of a heart are loaded into memory and in block 320, the video clip imagery in the set are filtered to include only one or more selected views of images acquired according to a selected modality. Then, in block 330 the filtered video clip imagery each are corrected through cropping, padding or rotation functions. Finally, a subset of the filtered video clip imagery is selected in block 340 as input in block 350 to the neural network. Optionally, a particular neural network trained in association with the selected views and selected modality is selected to receive the input in block 350. In decision block 360, it is determined if the neural network is able to output an ejection fraction. If so, the ejection fraction is displayed in block 390. Otherwise, in decision block 370 it is determined if additional images remain to be processed by the neural network. If so, an additional subset of the filtered images is selected in block 340 for as input in block 350 to the neural network. If no further images remain to be processed, an error condition results in block 380.

The present invention may be embodied within a system, a method, a computer program product or any combination thereof. The computer program product may include a computer readable storage medium or media having computer readable program instructions thereon for causing a processor to carry out aspects of the present invention. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing.

Computer readable program instructions described herein can be downloaded to respective computing/processing devices from a computer readable storage medium or to an external computer or external storage device via a network. The computer readable program instructions may execute entirely on the user's computer, partly on the user's computer, as a stand-alone software package, partly on the user's computer and partly on a remote computer or entirely on the remote computer or server. Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which includes one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Finally, the terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes" and/or "including," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Having thus described the invention of the present application in detail and by reference to embodiments thereof, it will be apparent that modifications and variations are possible without departing from the scope of the invention defined in the appended claims as follows:

We claim:

1. A method for artificially intelligent ejection fraction determination, the method comprising:
    training a neural network with different sets of cardiac imaging data acquired of a ventricle for different hearts and a known ejection fraction for each of the sets;
    loading the trained neural network into memory of a computer;
    acquiring a contemporaneous set of imaging data of a ventricle of a heart;
    providing the contemporaneous set of imaging data to the neural network; and,
    displaying in a display of the computer an ejection fraction determination output by the neural network without tracing a ventricle boundary of the heart.

2. The method of claim 1, further comprising filtering the acquired contemporaneous set of imaging data to only imaging data pertaining to video clips acquired utilizing a specified modality of imaging and representing a specific view of the ventricle.

3. The method of claim 1, wherein:
    only a portion of the contemporaneous set of imaging data is provided to the neural network; and,
    upon receiving an indication from the neural network of an inconclusive output, providing an additional portion of the contemporaneous set of imaging data to the neural network in order to receive a conclusive ejection fraction output from the neural network.

4. The method of claim 1, further comprising:
    training a multiplicity of different neural networks with different sets of cardiac imaging data acquired of the ventricle for different hearts and a known ejection fraction for each of the sets utilizing respectively different views and modalities;
    loading a particular one of the trained neural networks into the memory of the computer corresponding to an identified modality and at least one specified view of the contemporaneous set of imaging data.

5. The method of claim 1, further comprising pre-processing the contemporaneous set of imaging data in the form of video clip imagery through re-sizing and cropping of each video clip in the video clip imagery.

6. The method of claim 1, wherein providing the contemporaneous set of imaging data to the neural network comprises decomposing each video clip of the contemporaneous set of imaging data when in the form of video clip imagery into a multiplicity of frames of a movie clip and repeatedly submitting the frames, in parallel, to the neural network.

7. An cardiographic data processing system configured for artificially intelligent ejection fraction determination, the system comprising:
    a host computing platform comprising one or more computers each with memory and at least one processor; and,
    an ejection fraction determination module comprising computer program instructions enabled upon execution in the memory of the host computing platform to perform:
        training a neural network with different sets of cardiac imaging data acquired of a ventricle for different hearts and a known ejection fraction for each of the sets;
        loading the trained neural network into the memory;
        acquiring a contemporaneous set of video clip imagery of a ventricle of a heart;
        providing the contemporaneous set of imaging data to the neural network; and,
        displaying in a display of at least one of the computers an ejection fraction determination output by the neural network without tracing a ventricle boundary of the heart.

8. The system of claim 7, further comprising filtering the acquired contemporaneous set of imaging data to only imaging data pertaining to video clips acquired utilizing a specified modality of imaging and representing a specific view of the ventricle.

9. The system of claim 7, wherein:
    only a portion of the contemporaneous set of imaging data is provided to the neural network; and,
    upon receiving an indication from the neural network of an inconclusive output, providing an additional portion of the contemporaneous set of imaging data to the neural network in order to receive a conclusive ejection fraction output from the neural network.

10. The system of claim 7, wherein the computer program instructions are further enabled upon execution in the memory of the host computing platform to perform:
    training a multiplicity of different neural networks with different sets of cardiac imaging data acquired of the ventricle for different hearts and a known ejection fraction for each of the sets utilizing respectively different views and modalities;
    loading a particular one of the trained neural networks into the memory of the computer corresponding to an identified modality and at least one specified view of the contemporaneous set of imaging data.

11. The system of claim 7, wherein the computer program instructions are enabled upon execution in the memory of the host computing platform to further perform pre-processing the contemporaneous set of imaging data in the form of video clip imagery through re-sizing and cropping of each video clip in the video clip imagery.

12. The system of claim 7, wherein the computer program instructions providing the contemporaneous set of imaging data to the neural network comprises computer program instructions for decomposing each video clip of the contemporaneous set of imaging data when in the form of video clip imagery into a multiplicity of frames of a movie clip and repeatedly submitting the frames, in parallel, to the neural network.

13. A computer program product for artificially intelligent ejection fraction determination, the computer program product including a computer readable storage medium having program instructions embodied therewith, the program instructions executable by a device to cause the device to perform a method including:
    training a neural network with different sets of cardiac imagery acquired of a ventricle for different hearts and a known ejection fraction for each of the sets;
    loading the trained neural network into memory of a computer;
    acquiring a contemporaneous set of imaging data of a ventricle of a heart;
    providing the contemporaneous set of imaging data to the neural network; and, displaying in a display of the computer an ejection fraction determination output by the neural network without tracing a ventricle boundary of the heart.

14. The computer program product of claim 13, further comprising filtering the acquired contemporaneous set of imaging data to only imaging data pertaining to video clips acquired utilizing a specified modality of imaging and representing a specific view of the ventricle.

15. The computer program product of claim 13, wherein:
   only a portion of the contemporaneous set of imaging data is provided to the neural network; and,
   upon receiving an indication from the neural network of an inconclusive output, providing an additional portion of the contemporaneous set of imaging data to the neural network in order to receive a conclusive ejection fraction output from the neural network.

16. The computer program product of claim 13, further comprising:
   training a multiplicity of different neural networks with different sets of cardiac imaging data acquired of the ventricle for different hearts and a known ejection fraction for each of the sets utilizing respectively different views and modalities;
   loading a particular one of the trained neural networks into the memory of the computer corresponding to an identified modality and at least one specified view of the contemporaneous set of imaging data.

17. The computer program product of claim 13, wherein the method further comprises pre-processing the contemporaneous set of imaging data in the form of video clip imagery through re-sizing and cropping of each of the video clips in the video clip imagery.

18. The computer program product of claim 13, wherein providing the contemporaneous set of video clip imagery to the neural network comprises decomposing each video clip of the contemporaneous set of imaging data when in the form of video clip imagery into a multiplicity of frames of a movie clip and repeatedly submitting the frames, in parallel, to the neural network.

* * * * *